United States Patent
Huizenga et al.

(10) Patent No.: US 10,221,116 B2
(45) Date of Patent: Mar. 5, 2019

(54) PROCESS FOR THE SEPARATION OF MONOETHYLENE GLYCOL AND 1,2-BUTANEDIOL

(71) Applicant: SHELL OIL COMPANY, Houston, TX (US)

(72) Inventors: Pieter Huizenga, Amsterdam (NL); Charles-Edouard Sanders, Gyeongsangnam-do (KR)

(73) Assignee: SHELL OIL COMPANY, Houston, TX (US)

( * ) Notice: Subject to any disclaimer, the term of this patent is extended or adjusted under 35 U.S.C. 154(b) by 327 days.

(21) Appl. No.: 15/300,506

(22) PCT Filed: Apr. 2, 2015

(86) PCT No.: PCT/EP2015/057320
§ 371 (c)(1),
(2) Date: Sep. 29, 2016

(87) PCT Pub. No.: WO2015/150520
PCT Pub. Date: Oct. 8, 2015

(65) Prior Publication Data
US 2017/0174596 A1    Jun. 22, 2017

(30) Foreign Application Priority Data

Apr. 2, 2014    (EP) .................................... 14163242

(51) Int. Cl.
*C07C 29/82* (2006.01)
*B01D 3/14* (2006.01)
(Continued)

(52) U.S. Cl.
CPC .............. *C07C 29/82* (2013.01); *B01D 3/143* (2013.01); *B01D 3/36* (2013.01)

(58) Field of Classification Search
CPC ....... C07C 29/82; C07C 31/20; C07C 31/202; B01D 3/14; B01D 3/36; B01D 3/143
See application file for complete search history.

(56) References Cited

U.S. PATENT DOCUMENTS

| 2,831,801 A | 4/1958 | Beckham et al. |
| 4,032,583 A | 6/1977 | Arganbright et al. |
| (Continued) | | |

FOREIGN PATENT DOCUMENTS

| CN | 102643165 | 8/2012 |
| CN | 103396290 | 11/2013 |
| (Continued) | | |

OTHER PUBLICATIONS

Zeitsch, Karl J.:The chemistry and technology of furfural and its many by-products. sugar series, 13, Elsevier, 2000.
(Continued)

*Primary Examiner* — Brian A McCaig

(57) ABSTRACT

The invention provides a process for separating monoethylene glycol from a mixture comprising monoethylene glycol and 1,2-butanediol, said process comprising the steps of: a. providing a first stream comprising monoethylene glycol and 1,2-butanediol to a first distillation zone operated at a first pressure and under conditions to remove a first bottoms stream comprising 1,2-butanediol and to remove a first azeotrope of monoethylene glycol and 1,2-butanediol from the first distillation zone as a first overheads stream; b. withdrawing said first overheads stream from said first distillation zone; and c. providing said first overheads stream to a second distillation zone operated at a second pressure higher than said first pressure and under conditions to remove a second bottoms stream comprising monoethylene glycol and providing a second azeotrope of monoethylene glycol and 1,2-butanediol as a second overheads stream; d. withdrawing said second overheads stream from the second (Continued)

distillation zone and providing it to the first distillation zone as at least a portion of the first stream comprising monoethylene glycol and 1,2-butanediol, e. wherein the mixture comprising monoethylene glycol and 1,2-butanediol is initially provided to at least one of the first distillation zone and the second distillation zone.

9 Claims, 2 Drawing Sheets

(51) Int. Cl.
  *B01D 3/36* (2006.01)
  *C07C 31/20* (2006.01)

(56) References Cited

U.S. PATENT DOCUMENTS

| | | | |
|---|---|---|---|
| 4,081,354 A | 3/1978 | Christman | |
| 4,447,643 A | 5/1984 | Feldman | |
| 4,966,658 A | 10/1990 | Berg | |
| 5,387,731 A | 2/1995 | Jenkins et al. | |
| 5,423,955 A | 6/1995 | Berg | |
| 6,023,003 A | 2/2000 | Dunning et al. | |
| 2005/0072663 A1 | 4/2005 | Laborie et al. | |
| 2009/0171129 A1 | 7/2009 | Evanko et al. | |
| 2010/0317902 A1* | 12/2010 | Liu | C07C 29/80 568/868 |
| 2011/0312050 A1 | 12/2011 | Zhang et al. | |
| 2012/0018293 A1 | 1/2012 | Kaasa et al. | |
| 2012/0184783 A1 | 7/2012 | Barnicki | |
| 2013/0284584 A1 | 10/2013 | Xiao et al. | |

FOREIGN PATENT DOCUMENTS

| | | |
|---|---|---|
| CN | 103664522 | 3/2014 |
| CN | 103772147 | 5/2014 |
| CN | 103772148 | 5/2014 |
| EP | 844228 | 5/1998 |
| JP | 2009256294 | 11/2009 |
| WO | 1995019946 | 7/1995 |
| WO | 2004052808 | 6/2004 |
| WO | 2010080038 | 7/2010 |
| WO | 2011028131 | 3/2011 |
| WO | 2012130316 | 10/2012 |
| WO | 2013011462 | 1/2013 |

OTHER PUBLICATIONS

Garcia-Chavez, et al.; "COSMO-RS assisted solvent screening for liquid-liquid extraction of mono ethylene glycol from aqueous streams", Separation and Purification Technology, vol. 97, Sep. 3, 2012, pp. 2-10, XP002716373.

Lange, Jean-Paul, et al.: Furfural-A Promisign Platform for Lignocellulosic Biofuels, ChemSusChem 2012, pp. 150-166.

Watson, James M., et al.:Butane-1,4-diol from Hydrolytic Reduction of Furan, Ind. Eng. Chem. Prod. Res. Develop., vol. 12, No. 4, pp. 310-311, 1973.

Hoydonckx, H.E, et al.: Furfural and Derivatives, in Ulmann' s Encyclopedia or Industrial Chemistry, vol. 16, pp. 285-313, 2012.

Knapp, Jeffrey P., et al.: A New Pressure-Swing-Distillation Process for Separating Homogeneous Azeotropic Mixtures, Ind. Eng. Chem. Res. 3vol. 31, No. 1, pp. 346-357, 1992.

* cited by examiner

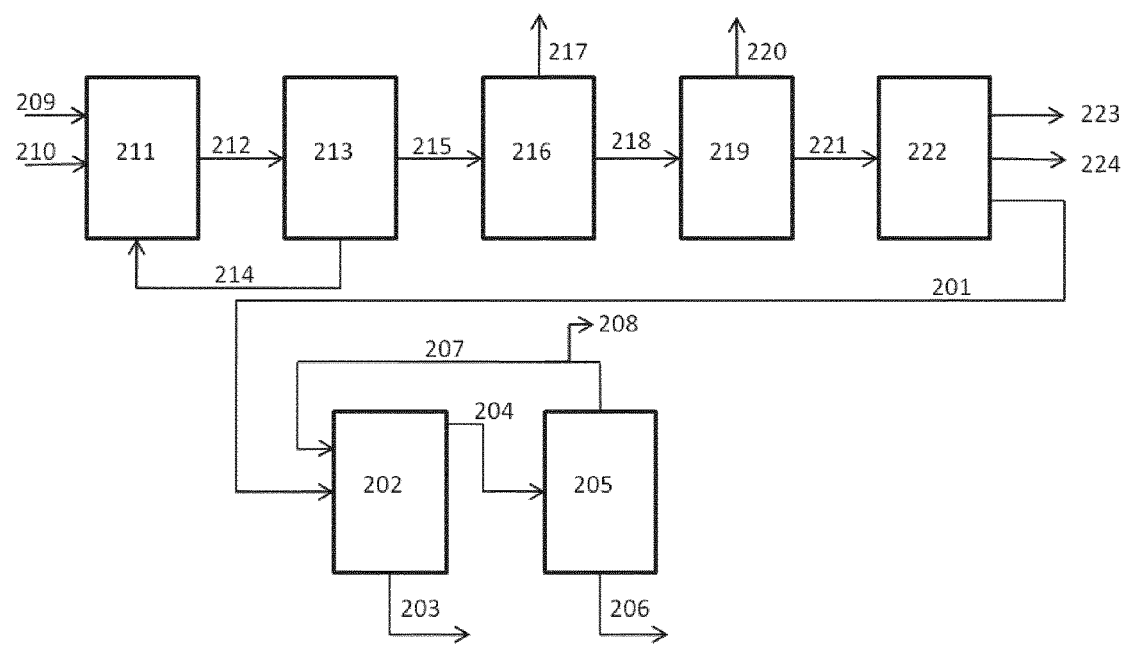

PROCESS FOR THE SEPARATION OF MONOETHYLENE GLYCOL AND 1,2-BUTANEDIOL

PRIORITY CLAIM

The present application is a National Stage (§ 371) application of PCT/EP2015/057320, filed 2 Apr. 2015, which claims priority from European patent Application 14163242.2 filed 2 Apr. 2014, each of which are hereby incorporated by reference in their entirety.

FIELD OF THE INVENTION

The present invention relates to a process for the separation of monoethylene glycol and 1,2-butanediol.

BACKGROUND OF THE INVENTION

Monoethylene glycol and propylene glycol are valuable materials with a multitude of commercial applications, e.g. as heat transfer media, antifreeze, and precursors to polymers, such as PET. Monoethylene and propylene glycols are typically made on an industrial scale by hydrolysis of the corresponding alkylene oxides, which are the oxidation products of ethylene and propylene, produced from fossil fuels.

In recent years, increased efforts have focused on producing chemicals, including glycols, from renewable feedstocks, such as sugar-based materials. For example, US 2011/312050 describes a continuous process for the catalytic generation of polyols from cellulose, in which the cellulose is contacted with hydrogen, water and a catalyst to generate an effluent stream comprising at least one polyol.

CN 102643165 is directed to a catalytic process for reacting sugar in an aqueous solution with hydrogen in the presence of a catalyst in order to generate polyols.

As with many chemical processes, the reaction product streams in these reactions comprise a number of desired materials, diluents, by-products and other undesirable materials. In order to provide a high value process, the desirable product or products must be obtainable from the reaction product stream in high purity with a high percentage recovery of each product and with as low as possible use of energy and complex equipment.

In known processes to make glycols, such as the hydrolysis of ethylene oxide, the glycols are usually present at high dilution in a solvent, typically water. The water is usually removed from the glycols by distillation. Subsequent purification of the glycols is then carried out by fractional distillation.

When glycols are produced by hydrogenolysis of sugars or sugar alcohols, a mixture of glycols is produced. The main glycol constituents in the reaction product stream are monoethylene glycol (MEG), monopropylene glycol (MPG) and 1,2-butanediol (1,2-BDO). The separation of these glycols by fractional distillation is problematic due to the similarity in boiling points, particularly between MEG and 1,2-BDO. The necessary specification for commercial fibre-grade MEG is 99.6 wt % purity. Other grades, such as the lower-value solvent grade MEG (98+wt %) do also exist. It is impossible to recover a high proportion of the MEG at either of these levels of purity from a mixture of MEG and 1,2-BDO by fractional distillation alone due to the formation of MEG/1,2-BDO azeotropes at pressures at which the temperatures required for distillation would not result in the decomposition of glycols. Different methods for the separation on MEG and 1,2-BDO are, therefore, required.

U.S. Pat. No. 4,966,658 is directed to the separation of a mixture of 1,2-BDO and MEG using a process known as azeotropic distillation in which an azeotrope-forming agent is added to the mixture before distillation in order to facilitate separation. A similar process is described in U.S. Pat. No. 5,423,955 for the separation of 1,2-BDO and MPG. Azeotropic distillation can lead to an increase in relative volatility between the components but also leads to further process steps in order to remove the azeotrope forming agents.

The potential application of pressure swing distillation to a number of pressure sensitive binary azeotropes is described in J. P. Knapp and M. F. Doherty, Ind. Eng. Chem. Res., 1992, 31, 346-357. The application of this process to glycols is not described.

WO 2004052808 is directed to a process for the separation of tertiary butyl alcohol from diisobutylene using pressure swing distillation. In said process a mixture of tertiary butyl alcohol and diisobutylene is fed to a first column from which diisobutylene is removed as a bottoms stream. An azeotrope of diisobutylene and tertiary butyl alcohol is also removed from the first column and is then fed to a second column operating at a lower pressure allowing tertiary butyl alcohol to be removed as a bottoms stream.

It would be advantageous to provide an improved method suitable for the separation of monoethylene glycol and 1,2-butanediol from a mixture containing these two components.

SUMMARY OF THE INVENTION

Accordingly, the present invention provides a process for separating monoethylene glycol from a mixture comprising monoethylene glycol and 1,2-butanediol, said process comprising the steps of:
(a) providing a first stream comprising monoethylene glycol and 1,2-butanediol to a first distillation zone operated at a first pressure and under conditions to remove a first bottoms stream comprising 1,2-BDO and to provide a first azeotrope of monoethylene glycol and 1,2-butanediol from the first distillation zone as a first overheads stream;
(b) withdrawing said first overheads stream from said first distillation zone;
(c) providing said first overheads stream to a second distillation zone operated at a second pressure higher than said first pressure and under conditions to remove a second bottoms stream comprising monoethylene glycol and providing a second azeotrope of monoethylene glycol and 1,2-butanediol as a second overheads stream;
(d) withdrawing said second overheads stream from the second distillation zone and providing it to the first distillation zone as at least a portion of the first stream comprising monoethylene glycol and 1,2-butanediol, wherein the mixture comprising monoethylene glycol and 1,2-butanediol is initially provided to at least one of the first distillation zone and the second distillation zone.

BRIEF DESCRIPTION OF THE DRAWINGS

FIGS. 1 and 2 are schematic diagrams of exemplary, but non-limiting, embodiments of a process for the separation of alcohols as described herein.

DETAILED DESCRIPTION OF THE INVENTION

Figure 1:
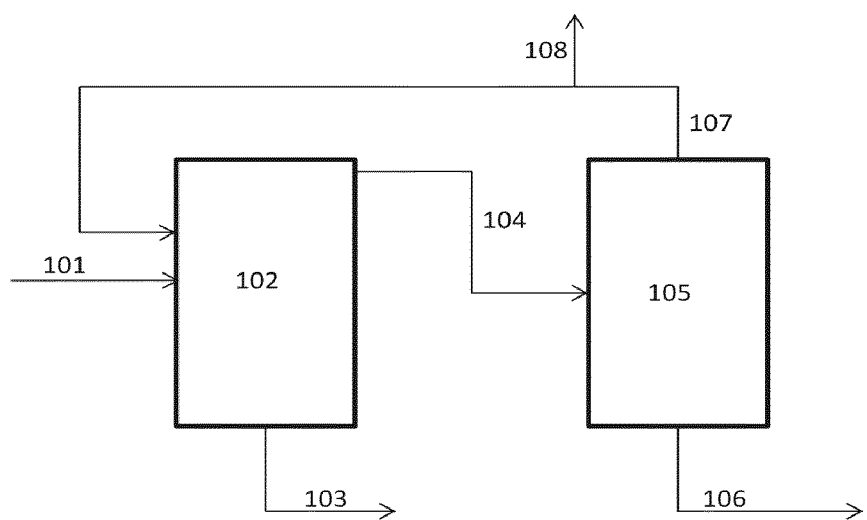

The present inventors have surprisingly found that MEG and 1,2-BDO can be separated from a stream comprising these two components using a two column pressure swing distillation system. In this system, 1,2-BDO is produced as the bottoms stream from a first distillation column operating at a lower pressure, the resultant azeotrope being fed to a second distillation column operating at a higher pressure, from which MEG is produced as the bottoms stream. The MEG stream produced is preferably at least 99.6 wt % MEG.

Preferably, the mixture comprising monoethylene glycol and 1,2-butanediol is derived from the reaction product stream from a process for the hydrogenolysis of a saccharide-containing or sugar alcohol-containing feedstock.

In such a reaction product stream, the MEG and 1,2-BDO are typically present at a combined concentration in the range of from 0.1 to 30 wt %.

As well as the MEG and 1,2-BDO, the reaction product stream from a hydrogenolysis reaction of saccharides or sugar alcohols may comprise other glycols, such as MPG and 2,3-butanediol (2,3-BDO), water, oxygenates, hydrocarbons, catalyst, degradation products, and gases in any composition. The variety of compounds and their concentration depend on the feedstock and the various hydrogenation and hydrogenolysis conversion conditions, including catalysts, reaction conditions such as temperature, pressure and saccharide concentration.

Before undergoing the process of the present invention, the reaction product stream from a process for the hydrogenolysis of a saccharide or sugar alcohol containing feedstock suitably undergoes a number of purification steps in order to provide the stream comprising monoethylene glycol and 1,2-butanediol.

Such steps may include the removal of any catalyst present, for example by filtration; removal of gases and light ends, for example by phase separation; and removal of water, for example by distillation. Further purification of the stream comprising monoethylene glycol and 1,2-butanediol may then be carried out by separating off the other remaining organic components. In one embodiment of the process, separation of the remaining organic components is achieved by a multi-stage distillation process in order to remove heavy hydrocarbons and oxygenates and separate other glycols such as MPG and 2,3-butanediol (2,3-BDO). In an alternative embodiment of the process, a mixture comprising at least MEG and 1,2-BDO may be separated from the other remaining organic components using an extracting liquid, which may then, subsequently, be removed from the mixture.

The resultant stream comprising monoethylene glycol and 1,2-butanediol preferably comprises at least 35 wt %, more preferably at least 50 wt %, even more preferably at least 70 wt %, even more preferably at least 80 wt %, most preferably at least 90 wt % MEG. The resultant stream comprising monoethylene glycol and 1,2-butanediol preferably comprises at least 0.1 wt %, more preferably at least 0.4 wt %, most preferably at least 1 wt % and preferably at most 65 wt %, more preferably at most 50 wt %, even more preferably at most 30 wt %, most preferably at most 20 wt % 1,2-BDO. Possible other constituents in the stream comprising monoethylene glycol and 1,2-butanediol include diols such as MPG, 1,3-propanediol and 2,3-BDO. Suitable other constituents make up at most 20 wt %, preferably at most 10 wt % of the stream comprising monoethylene glycol and 1,2-butanediol.

In the process of the invention the first distillation zone preferably comprises a first distillation column. Said first distillation column preferably comprises at least 40 stages, more preferably at least 50 stages, most preferably at least 55 stages and preferably at most 80 stages, more preferably at most 70 stages, most preferably at most 80 stages, for example 60 stages.

A stage is a hypothetical zone within a distillation column in which a vapour-liquid equilibrium is established. The number of stages may be linked to the number of trays by the tray efficiency and in a packed column the height equivalent to a theoretical plate (HETP) may be used. One skilled in the art would readily be able to convert between these features.

The first stream comprising monoethylene glycol and 1,2-butanediol may be fed to the first distillation column at any convenient point. Preferably, the first stream comprising monoethylene glycol and 1,2-butanediol is fed to the first distillation column at a point at least 25, more preferably at least 30, even more preferably at least 32 stages from the top of the column. Preferably, the stream comprising monoethylene glycol and 1,2-butanediol is fed to the first distillation column at a point at most 45, more preferably at most 40, even more preferably at most 38 stages from the top of the column. For example, the stream comprising monoethylene glycol and 1,2-butanediol may be fed to the first distillation column at a point 35 stages below the top of the column.

The first pressure is preferably at least 0.7 kPa, more preferably at least 1.0 kPa. The first pressure is preferably at most 10 kPa, more preferably at most 5 kPa, most preferably at most 4 kPa. Suitable conditions in the first distillation zone include a temperature of at least 90° C., preferably at least 105° C., most preferably at least 115° C. and at most 145° C., preferably at most 130° C., more preferably at most 120° C.

The first bottoms stream comprises 1,2-BDO. Said first bottoms stream preferably comprises at least 10 wt %, more preferably at least 50 wt %, most preferably at least 90 wt % of 1,2-BDO on the basis of the overall weight of the first bottoms stream.

This stream may be further purified in order to obtain high purity 1,2-BDO or a derivative thereof. However, it may also be disposed of, burned, used as a fuel or as a blending component in fuels.

The first overheads stream is removed from the first distillation zone and comprises a first azeotrope of MEG and 1,2-BDO. Suitably, the first azeotrope comprises MEG and 1,2-BDO in a ratio of MEG:1,2-BDO in the range of from 5:1 to 20:1.

The first overhead stream is fed to a second distillation zone. The second distillation zone preferably comprises a second distillation column. Said second distillation column preferably comprises at least 40 stages, more preferably at least 50 stages, most preferably at least 55 stages and preferably at most 80 stages, more preferably at most 70 stages, most preferably at most 80 stages, for example 60 stages.

The first overheads stream may be fed to the second distillation column at any convenient point. Preferably, the first overheads stream is fed to the second distillation column at a point at least 5, more preferably at least 8 stages from the top of the column. Preferably, the first overheads stream is fed to the second distillation column at a point at most 20, more preferably at most 15, even more preferably at most 13 stages from the top of the column. For example, the first overheads stream may be fed to the second distillation column at a point 10 stages below the top of the column.

The second pressure is preferably at least 50 kPa, more preferably at least 90 kPa, most preferably at least 100 kPa. The second pressure is preferably at most 150 kPa, more preferably at most 120 kPa. Suitable conditions in the second distillation zone include a temperature of at least 160° C., preferably at least 180° C. and at most 220° C., preferably at most 200° C.

MEG is removed as a second bottoms stream. Said second bottoms stream preferably comprises at least 95 wt %, more preferably at least 98 wt %, most preferably at least 99.6 wt % of MEG based on the overall weight of the second bottoms stream.

The second overheads stream comprises a second azeotrope of MEG and 1,2-BDO. Said second azeotrope comprises less MEG than the first azeotrope. Suitably, the second azeotrope comprises MEG and 1,2-BDO in a ratio of MEG: 1,2-BDO in the range of from 3:1 to 4:1.

In the process of the invention, the second overheads stream is withdrawn from the second distillation zone comprising a second distillation column and fed to the first distillation zone comprising a first distillation column, providing at least a portion of the first stream comprising monoethylene glycol and 1,2-butanediol. This allows continuous recycling of the azeotropes and purification of the maximum amount of the desired products, particularly MEG. The second overheads stream may be fed to the first distillation column at any convenient point. Preferably, the second overheads stream is fed to the first distillation column at a point at least 10, more preferably at least 17 stages from the top of the column. Preferably, the second overheads stream is fed to the first distillation column at a point at most 30, more preferably at most 25, even more preferably at most 23 stages from the top of the column. For example, the second overheads stream may be fed to the first distillation column at a point 20 stages below the top of the column.

The mixture comprising monoethylene glycol and 1,2-butandiol is initially provided to at least one of the first distillation zone and the second distillation zone. Initially provided is used herein to refer to providing a fresh feed of the mixture comprising monoethylene glycol and 1,2-butandiol, which has not been subjected to either of the distillation zones, to the process of the invention.

The mixture comprising monoethylene glycol and 1,2-butanediol may be initially provided as part of one of the feed streams to the distillation zones, e.g. the first overheads stream or the first stream comprising monoethylene glycol and 1,2-butanediol. Alternatively, the mixture comprising monoethylene glycol and 1,2-butanediol may be initially provided to either of the first or second distillation zones as a separate feed.

In the embodiment wherein the mixture comprising monoethylene glycol and 1,2-butanediol is initially provided to either of the first or second distillation zones as a separate feed, this separate feed may be fed to the either column at any convenient point.

Preferably, if the separate feed is fed to the first distillation column, it is fed at a point at least 25, more preferably at least 30, even more preferably at least 32 stages from the top of the column. Preferably, if the separate feed is fed to the first distillation column, it is fed is fed to the first distillation column at a point at most 45, more preferably at most 40, even more preferably at most 38 stages from the top of the column. For example, the separate feed may be fed to the first distillation column at a point 35 stages below the top of the column.

Preferably, if the separate feed is fed to the second distillation column, it is fed at a point at least 5, more preferably at least 8 stages from the top of the column. Preferably, if the separate feed is fed to the second distillation column, it is fed at a point at most 20, more preferably at most 15, even more preferably at most 13 stages from the top of the column. For example, the separate feed may be fed to the second distillation column at a point 10 stages below the top of the column.

Optionally, a bleed stream may be taken from either or both of the first or second overheads stream, preferably the second overheads stream, in order to prevent a build up of any unwanted components in the stream and to reduce the size of the recycle. Such a bleed stream or streams preferably comprises at most 10 wt % more preferably 5 wt % of the overall first or second overheads streams.

In a particularly preferred, but non-limiting, embodiment of the invention illustrated in FIG. 1, a mixture comprising monoethylene glycol and 1,2-butandiol 101 is initially fed to a first distillation column 102. A first bottoms stream comprising 1,2-BDO 103 is removed and a first overheads stream 104 is fed to a second distillation zone 105. A second bottoms stream comprising MEG 106 is removed. A second azeotrope of MEG and 1,2-BDO is removed as a second overheads stream 107 and recycled as the first stream comprising monoethylene glycol and 1,2-butandiol provided to the first distillation zone 102. An optional bleed stream 108 is shown providing a bleed from the second overheads stream.

A further preferred, but non-limiting, embodiment is shown in FIG. 2. A saccharide-containing feedstock 209 is fed to a reactor 211 and reacted with a hydrogen feed 210 in the presence of a catalyst and water. The resultant reaction product stream 212 is provided to a filtration unit 213 wherein solids comprising catalyst particles 214 are removed and recycled to the reactor 211. The resultant stream 215 is then fed to a light ends removal unit 216, where gases and other light ends 217 are removed. The remaining aqueous stream 218 is then processed in a water removal unit 219, to remove water 220 before being fed as a stream 221 to a organics separation unit 222 to provide one or more streams of organics represented as 223 and 224 and the stream comprising monoethylene glycol and 1,2-butanediol 201. This is then processed as described in FIG. 1. In an alternative embodiment, at least a part of the section of the process illustrated by water removal unit 219 and organics separation unit 222 may be replaced by an extraction unit in which organics comprising monoethylene glycol and 1,2-butanediol are extracted from the aqueous stream 218 using a solvent which is subsequently removed by distillation.

The present invention is further illustrated in the following Examples.

Examples

The process shown in FIG. 1 was simulated in a flow-sheeting programme, AspenPlus, licensed by Aspentech. Two RadFrac columns were used to simulate the distillation columns. This resulted in the following mass balance for the streams indicated in FIG. 1 and may serve as an illustrative example of the separation process. For simplicity, only components with a concentration greater than 1 ppm are shown in Table 1 below.

TABLE 1

(All numbers have been changed)

| | Stream | | | | | |
|---|---|---|---|---|---|---|
| | 101 | 103 | 104 | 106 | 107 | 108 |
| Temperature in ° C. | 116.4 | 87.7 | 83.2 | 211.9 | 206.2 | 206.2 |
| Pressure in bara | 0.05 | 0.01 | 0.01 | 1.5 | 1.5 | 1.5 |
| Mass flow in ktonne/year | 449.2 | 47.1 | 962.3 | 393.4 | 571.6 | 11.4 |
| | Mass fraction | | | | | |
| Ethylene Glycol | 91.8% | 36.3% | 71.3% | 99.6% | 51.9% | 51.9% |
| 1,2-Propylene glycol | 0.9% | | 21.3% | 1 ppm | 35.8% | 35.8% |
| 1,3-Propylene glycol | 0.4% | 4.3% | | | | |
| 1,4-butanediol | 14 ppm | 134 ppm | | | | |
| 1,3-butanediol | 1% | 7.2% | 0.1% | 41 ppm | 413 ppm | 413 ppm |
| 2,3-Butanediol | | | | | | |
| 1,2-Butanediol | 4.6% | 41.4% | 6.9% | 0.4% | 11.5% | 11.5% |
| 1,2-Pentanediol | 0.6% | 5.4% | 112 ppm | | 5 ppm | 5 ppm |
| 1,2-Hexanediol | 0.2% | 2.1% | | | | |
| 2,3-Hexanediol | 218 ppm | 519 ppm | 0.4% | | 0.6% | 0.6% |
| 4,5-Octanediol | 20 ppm | 189 ppm | | | | |
| 1,5-Hexanediol | 0.3% | 1.9% | 491 ppm | 6 ppm | 87 ppm | 87 ppm |
| DEG | 2 ppm | 22 ppm | | | | |
| Hydroxyacetic acid (glycolic acid) | 10 ppm | 93 ppm | | | | |
| Lactic acid | 149 ppm | 0.1% | | | | |
| Levulinic acid | 0.1% | 1.2% | 12 ppm | | | |

That which is claimed is:

1. A process for separating monoethylene glycol from a mixture comprising monoethylene glycol and 1,2-butanediol, said process comprising the steps of:
   (a) providing a first stream comprising monoethylene glycol and 1,2-butanediol to a first distillation zone operated at a first pressure and under conditions to remove a first bottoms stream comprising 1,2-butanediol and to remove a first azeotrope of monoethylene glycol and 1,2-butanediol from the first distillation zone as a first overheads stream;
   (b) withdrawing said first overheads stream from said first distillation zone; and
   (c) providing said first overheads stream to a second distillation zone operated at a second pressure higher than said first pressure and under conditions to remove a second bottoms stream comprising monoethylene glycol and providing a second azeotrope of monoethylene glycol and 1,2-butanediol as a second overheads stream;
   (d) withdrawing said second overheads stream from the second distillation zone and providing it to the first distillation zone as at least a portion of the first stream comprising monoethylene glycol and 1,2-butanediol,
   (e) wherein the mixture comprising monoethylene glycol and 1,2-butanediol is initially provided to at least one of the first distillation zone and the second distillation zone.

2. A process according to claim 1, wherein the mixture comprising monoethylene glycol and 1,2-butanediol is derived from the reaction product stream from a process for the hydrogenolysis of a saccharide-containing or a sugar alcohol-containing feedstock.

3. A process according to claim 1, wherein the second bottoms stream comprises at least 99.6 wt % of MEG.

4. A process according to claim 1, wherein the first pressure is at least 0.7 kPa and at most 10 kPa.

5. A process according to claim 1, wherein the second pressure is at least 50 kPa and at most 150 kPa.

6. A process according to claim 1, wherein the first overheads stream comprises MEG and 1,2-BOD in a ratio of MEG:1,2-BDO in the range of from 5:1 to 20:1.

7. A process according to claim 1, wherein the second overheads stream comprises MEG and 1,2-BDO in a ratio of MEG:1,2-BDO in the range of from 3:1 to 4:1.

8. A process according to claim 1, wherein the temperature in the first distillation zone is at least 90° C. and at most 145° C.

9. A process according to claim 1, wherein the temperature in the second distillation zone is at least 160° C. and at most 220° C.

\* \* \* \* \*